(12) United States Patent
Plecha et al.

(10) Patent No.: US 12,420,068 B2
(45) Date of Patent: Sep. 23, 2025

(54) TORQUE DEVICE APPARATUS AND METHOD OF USE

(71) Applicant: Edward Plecha, San Diego, CA (US)

(72) Inventors: Edward Plecha, San Diego, CA (US); Matthew T. Fisher, Reno, NV (US)

(73) Assignee: Edward Plecha, San Diego, CA (US)

( * ) Notice: Subject to any disclaimer, the term of this patent is extended or adjusted under 35 U.S.C. 154(b) by 0 days.

(21) Appl. No.: 18/135,068

(22) Filed: Apr. 14, 2023

(65) Prior Publication Data
US 2023/0248948 A1  Aug. 10, 2023

Related U.S. Application Data

(63) Continuation of application No. 18/080,711, filed on Dec. 13, 2022.
(Continued)

(51) Int. Cl.
*A61M 25/09* (2006.01)
*A61M 39/02* (2006.01)

(52) U.S. Cl.
CPC .. *A61M 25/09041* (2013.01); *A61M 39/0247* (2013.01); *A61M 2025/09116* (2013.01);
(Continued)

(58) Field of Classification Search
CPC ........ A61M 25/09041; A61M 25/0113; A61M 2025/09116; A61M 39/0247; A61M 2039/0258; A61M 2039/0279
See application file for complete search history.

(56) References Cited

U.S. PATENT DOCUMENTS 5,755,695 A * 5/1998 Erickson ........... A61M 25/0136
604/905
6,235,001 B1   5/2001 O'Holloran et al.
(Continued)

FOREIGN PATENT DOCUMENTS

| EP | 1437154 | 7/2004 |
| WO | 2018093612 | 5/2018 |

OTHER PUBLICATIONS

International Search Report and Written Opinion of The International Searching Authority for International Application PCT/US23/11179, mailed Apr. 24, 2023.

*Primary Examiner* — Katherine M Rodjom
(74) *Attorney, Agent, or Firm* — Holland & Hart LLP

(57) ABSTRACT

A torque device useable in some embodiments in an endovascular procedure. The torque device is connectable to catheter end to provide an interlocked torque-device/catheter that can be mounted to, and slid over, a guidewire as a unit. A spring arm extends from a main body section of the torque device and can be depressed into the main body section so that the spring arm and main body section can be secured in position with respect to each other. In one embodiment, the depressed spring arm and main body section are mountable to an end of a catheter to secure them in position and to the catheter. Alternatively, the torque device can be mounted to a guide wire by depressing the spring arm, and releasing the spring arm can cause torque device to grip the guide wire and allow the operator to turn or move the torque device and gripped guide wire. Some embodiments provide a torque device through which material may be injected into a catheter to which the torque device is connected.

29 Claims, 21 Drawing Sheets

Related U.S. Application Data

(60) Provisional application No. 63/265,330, filed on Dec. 13, 2021.

(52) U.S. Cl.
CPC ............... *A61M 2039/0258* (2013.01); *A61M 2039/0279* (2013.01)

(56) References Cited

U.S. PATENT DOCUMENTS

| | | | |
|---|---|---|---|
| 6,752,800 | B1 | 6/2004 | Winston et al. |
| 7,011,635 | B1 * | 3/2006 | Delay ................. A61M 25/0113 604/528 |
| 2004/0006329 | A1 | 1/2004 | Scheu |
| 2005/0096566 | A1 * | 5/2005 | Arnott ............. A61M 25/09041 604/528 |
| 2007/0219467 | A1 | 9/2007 | Clark et al. |
| 2014/0203555 | A1 | 7/2014 | Frankland et al. |
| 2016/0114139 | A1 | 4/2016 | McArthur et al. |
| 2017/0072171 | A1 | 3/2017 | Gallacher et al. |
| 2020/0164177 | A1 | 5/2020 | Neoh et al. |
| 2021/0000493 | A1 | 1/2021 | Badadamath et al. |
| 2021/0031004 | A1 | 2/2021 | Valaie et al. |

* cited by examiner

TORQUE DEVICE APPARATUS AND METHOD OF USE

CROSS-REFERENCE TO RELATED APPLICATION

This application is a continuation of applicant's prior U.S. patent application Ser. No. 18/080,711, filed Dec. 13, 2022, and titled "Torque Device Apparatus and Method of Use," which claims priority through, and incorporates by reference, the applicant's prior U.S. provisional application, titled Torque Device and Method of Use, Ser. No. 63/265,330, filed Dec. 13, 2021.

FIELD OF TECHNOLOGY

This specification involves torque devices for use in endovascular procedures using guidewires and catheters and similar structures on humans and other creatures.

BRIEF DESCRIPTION OF SOME ASPECTS OF THE BACKGROUND

In modern medicine, medical procedures inside a blood vessel (endovascular procedures) often involve gaining access to an artery or vein through the skin (percutaneous access). An artery is a blood vessel that carries blood from the heart to the tissues, and a vein circulates blood from the tissues to the heart.

This process of gaining access to an artery or vein commonly commences with first gaining percutaneous access by inserting a needle into the blood vessel. An access wire is then inserted through the needle into the blood vessel and the needle is removed. Most commonly, this is followed by sliding a hemostatic sheath over the guide access wire so that the distal end of the sheath rests inside the blood vessel. The proximal end of the sheath is external to the patient's skin.

The proximal end of the sheath has a side arm consisting of tubing and a stop cock. The side arm is used to inject fluids into the blood vessel, most often blood thinner solutions or angiographic contrast solutions used for imaging of the inside of the vessel. The proximal end also has an in-line passage that contains a one-way valve to 1) allow introduction of catheters and wires into the blood vessel and 2) prevent bleeding from the sheath end.

After insertion of the hemostatic sheath, the initial access wire used for insertion is typically removed from the sheath penetrating the access blood vessel. Subsequently, a guidewire, that most commonly has an angled or curved end, is inserted into the sheath. This wire is then advanced into the access vessel using imaging techniques that are well known to those skilled in the art.

Next, the operator mounts a catheter (which has an end shaped to help navigate the blood vessels to the desired location) by sliding it over the guidewire into the inline passage of the sheath and then into the blood vessel. along the guidewire penetrating the blood vessel. At this point, the operator will frequently mount a torque device onto the proximal (external) end of the guide wire.

There are a variety of torque device designs but the most common have a central channel, or lumen. The proximal end of the guidewire is inserted into the lumen of the torque device. The torque device is then slid over the external portion of the wire and is positioned at a wire control point that is usually 5-10 cm from the proximal (external) end of the catheter.

The guidewires may be quite long-measuring up to 300 cm in length with the external portion frequently over 200 cm in length. During the process of catheter insertion and torque device placement over the guidewire, the operator must also ensure that the distal (internal) end of the guide wire does not move significantly inside the blood vessel. Once in position at guide wire control point, the torque device functions by allowing the operator to cause the torque device to firmly grip the external portion of guidewire at that point and turn or steer the angled guidewire tip in the desired direction. Navigating the distal angled guidewire tip to the final target vessel frequently involves making several (and often more) guide wire turns within the blood vessels, and requires catheters of different shapes to be substituted over the guidewire and several (and often more) removals and replacements of the torque device on the guide wire.

This procedure is somewhat analogous to following a series of roads to a final destination with multiple turns onto side streets that come off at different angles. To accomplish this objective, multiple catheter exchanges of catheters with differently shaped distal ends are frequently required. during the procedure. With the current technology, these catheter exchanges are a two-step process. First the torque device must be removed, by sliding it off of the external portion of the guidewire. Once the torque device is removed the, this process is repeated with the existing catheter on the guidewire.

To accomplish the catheter exchange, a pinch-pull technique is employed wherein which the operator's one hand pinches the guide wire 5-10 cm distal from the position of the torque device, and the other hand grasps the torque device is then slid back on the guidewire with the other hand until the two hands meet. The first hand is then moved back 5-10 cm and the process is repeated. Once the torque device is removed, the catheter is then removed from the sheath in the same fashion.

As previously mentioned, angiographic wires are up to 300 cm long, and the process of torque device and catheter removal can be tedious, as the operator must simultaneously maintain guidewire position within the blood vessel. Having to separately remove the torque device and catheter compounds the risk for wire movement and this can result in loss of guidewire position within the vessel and progress in the vessel navigation procedure. This can result in loss of progress is because loss of guidewire position within the vessel, and requires repeating the prior maneuvers to bring the guidewire through its previous location positions to the desired position where movement caused loss of that desired positioning.

When inserting the new catheter (as opposed to when removing a catheter described above), the insertion process is repeated with insertion of the new catheter, and then insertion of the torque device, over the guidewire in the two separate mounting and insertion steps. identified above. Again, there is the possibility of inadvertently pulling the wire back as with the prior process for removal process of the torque device and prior catheter. In addition, the process of separate removal and placement of the catheter and torque device is time consuming, causing increased consumption of labor and significant hospital resources, and increased risk of medical complications for the patient, especially during long, complex endovascular procedures.

Another challenge presented by prior art endovascular procedures is encountered when the wire is successfully introduced into a branch. blood vessel. It may be desirable at this point to rapidly advance the wire to the next branch to be selected branch blood vessel. The rapid advancement along this straight segment of vessel "road" is hindered by the most common torque devices, which because they require active hand pressure on the torque device in order to open the passageway in the torque device and allow the guide wire to pass freely through the lumen in the torque device. Thus, one hand is required to depress a section of the torque device while the other hand simultaneously advances the guidewire. Once the guidewire has reached the next branch to be selected branch blood vessel, the catheter is advanced to that position and then the torque device must be depressed by one hand to allow the other hand to move the torque device to the working position 5-10 cm from the proximal end of the catheter. This two-handed procedure takes time and presents risk of loss of control over desired wire positioning in a blood vessel.

Further, once the guide wire is advanced to the desired final blood vessel destination, the torque device must be walked, or slid off of, the guide wire followed by sliding the positioning-catheter off of the guide wire. This allows the therapeutic-catheter (typically a balloon catheter or stent delivery catheter) to then be mounted on the guide wire and slid into position. Yet again, loss of often difficultly-gained vessel location access positioning of the guide wire is not uncommon during this repeated positioning-catheter removal and therapeutic-catheter insertion process; and when such a loss occurs, the vessel location procedure must be repeated.

Finally, it is not uncommon to have multiple blood vessel lesions in series and then to therefore have to again navigate beyond the initial lesion location. This would require additional shaped catheters and guidewires and related insertion and removal procedures, with the accompanying difficulties noted above.

BRIEF SUMMARY OF SOME ASPECTS OF THIS SPECIFICATION

The applicant believes he has discovered the problems with the prior art techniques described above, or their severity, and therefore developed the related solutions and novel features described within this specification. In one aspect, the applicant has provided a torque device that interconnects with a catheter so that the resulting lumen passing through the torque-device/catheter unit can be moved along a guidewire, have the torque device grip the guide wire periphery when desired, or support injection of materials, such as fluid, into and through the torque device and catheter.

In some embodiments the torque device has a main body section having (i) a first lumen section extending within the main body section from a first end of the main body section toward an opposed second end of the main body section and (ii) a spring arm having a first end section extending from the main body section and a second end section opposite the first end section and biased away from the main body section. The second end section has at least a portion of a second lumen section depressable toward the main body section, so that the second end section and main body section are then interlockable to secure the second end section in a depressed position and provide a continuous main body section lumen comprising the first lumen section and second lumen section.

In some embodiments, the interlocked second end section and main body section are mountable to a catheter. In some embodiments, the second end section and main body section are mountable to a catheter so that the catheter secures the second end section and main body section in position with respect to the catheter. In some embodiments, the second spring arm lumen section and second end lumen section in the main body section are cooperatively mountable in the proximal end of a catheter.

Some instances have a second spring arm lumen section and second end lumen section in the main body section that are moveable with respect to each other to cooperatively provide a main body lumen. In some instances, the spring arm is further moveable with respect to the main body section to have the spring arm grip the outer periphery of a guide wire penetrating a lumen in the torque device.

In some applications, the main body section of the torque device includes a spring arm channel matingly receptive of the second spring arm end section. In some instances, the spring arm end section includes a seal mounting section receptive of an optional resilient seal to prevent material, such as fluid for example, in the torque device from leaking out of structure in the torque device.

In some embodiments, the second spring arm lumen section and second end lumen section in the main body section are moveable with respect to each other to cooperatively provide a Leur lock end connectable to a catheter. In some applications, the spring arm includes a finger pad that may be used to move the spring arm with respect to the main body section.

Certain torque devices can include a Luer lock section in the first lumen section extending within the main body section.

Some embodiments provide a method of using a torque device during an endovascular or similar procedure by docking the torque device to a catheter and sliding the torque-device/catheter unit with one hand along a guide wire penetrating a blood vessel. In some embodiments, releasing of pressure on the torque device can cause it to grip the guide wire periphery and allow rotation of the guide wire around its axis.

Some procedures include depressing a biased spring arm of the torque device to penetrate a mating channel in the main body section and interconnecting the depressed spring arm and main body section end to dock to a catheter. Some procedures include also releasing the biased spring arm to cause the spring arm to grip the guide wire and simultaneously rotate the guide wire around its axis by rotating the torque device around the guide wire axis.

Some procedures involve mounting the torque device to a catheter and, with one hand compressing the torque device, such as a spring arm in the torque device in some embodiments, and with other hand gripping free guide wire, causing the torque device and catheter and guide wire to move with respect to each other. Some embodiments involve using one hand to compress the torque-device to release a guide wire and another hand to grip the guide wire and accomplish relative movement of the torque device with respect to the guide wire, either by sliding the torque device along the guide wire or sliding the guide wire through the torque device.

In some embodiments, material, such as fluid, can be injected into the torque-device/catheter unit and through the catheter into a blood vessel.

There are other novel features and aspects of the present specification. They will become apparent as this specification proceeds.

In this regard, the scope of the invention is not be determined because a given feature is set forth in the Brief Summary or addresses an issue or problem identified in the prior brief Background section. Rather, the scope of the invention is to be determined by the scope of the claims as issued.

BRIEF DESCRIPTION OF THE DRAWINGS

The applicant's preferred and other embodiments are disclosed in association with the accompanying Figures in which.

DETAILED DESCRIPTION

Figure 1:
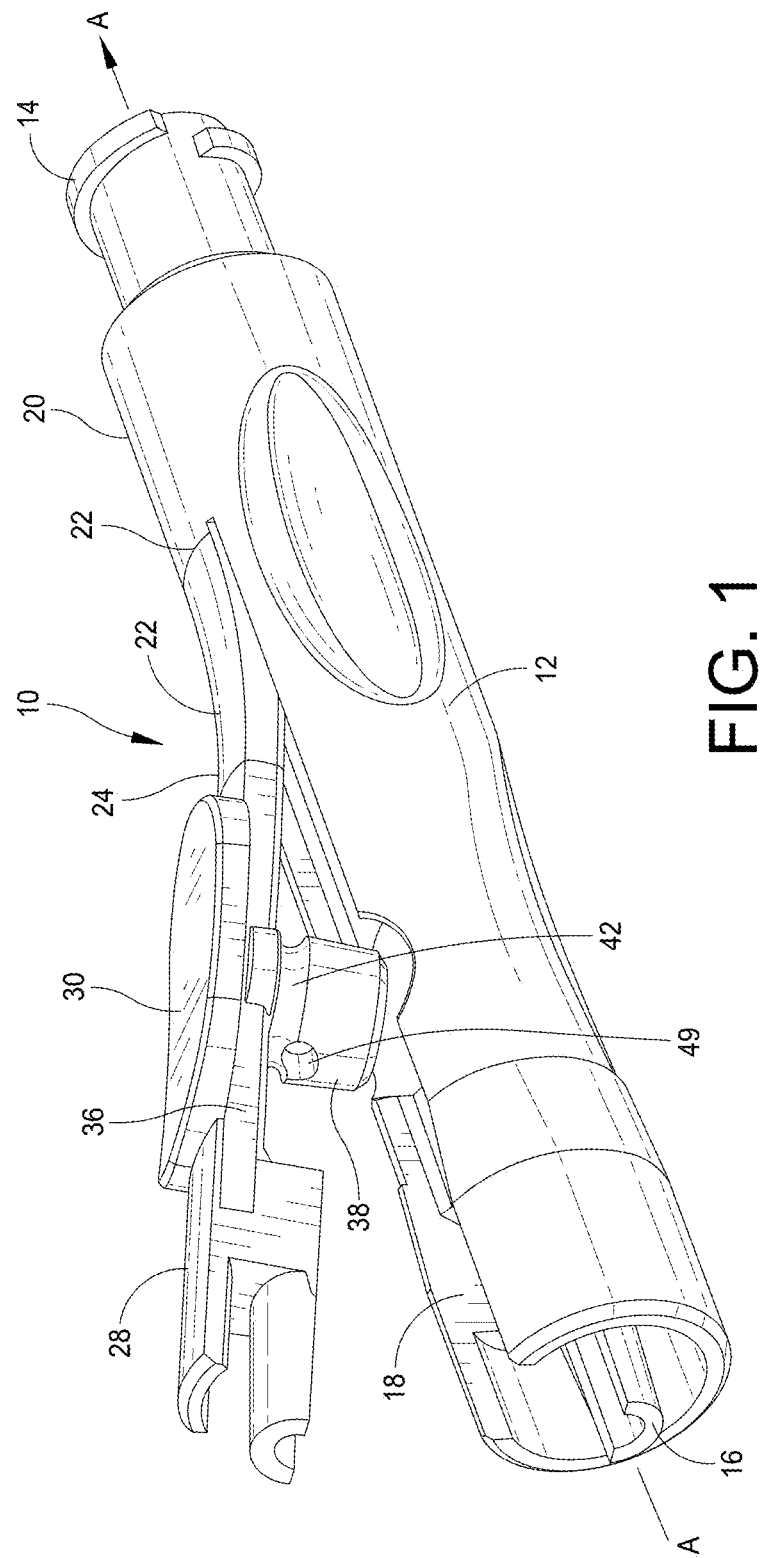
FIG. 1 is a grey-scale perspective first side view of an embodiment of the inventors' novel torque device showing its upper spring arm in an open, free, non-depressed, outwardly biased state.

The following description sets forth exemplary novel embodiments of the structure and method of use of the torque device of this specification. These descriptions of embodiments are not to limiting of the scope of the invention. Further, one or more features in these embodiments can be mixed and matched differently as desired; and similarly features can be deleted as desired.

With reference to FIGS. 1, 1A, 2, and 2A, an embodiment of the applicant's present, novel torque device 10 in its free-standing state has a somewhat cylindrical main body section 12 intermediate a first main body or rear or proximal end 14, which may be a connectable end or, more specifically in some embodiments, a narrowed female end 14, and an opposed second main body or front or distal end 16, which may be a connectable end or, more specifically, again, in some embodiments, a male end 16. The main body section 12 has a spring arm channel 18 (i) penetrating the partially cylindrical upper periphery 20 of the main body section 12 inwardly from its upper periphery 20 toward the laterally extending axis A-A of the main body section 12, and (ii) extending from a spring arm end 22 extending from the main body section 12 spaced from the rear or back female end 14 through the main body section 12 to penetrate its opposing front male lock end 16.

In this same torque device 10 free state, (i) a flexible and resilient spring arm 24 extends from the spring arm end 22 extending from the main body section 12 radially outwardly away from main body section 12 and its laterally extending axis A-A; and (ii) the spring arm 24 has an upwardly bending end 26 extending intermediate the spring arm end 22 and an opposed spring arm lever section 28 extending laterally away and upwardly from the upwardly bending end 26. The spring arm 24 has a widened, oblong, somewhat concave, disk-shaped finger-press section 30 extending laterally outwardly from the upper side 32 of the spring arm lever section 28 in a plane transverse to the opposed laterally extending planar sides 34, 36 of the spring arm lever section 28. The opposed laterally extending planar sides 34, 36 are parallel to each other in planes parallel to, and spaced at equal distances from, the lumen axis A-A of the main body section 12.

A partially cylindrical guide wire locking block 38 extends downwardly from the finger-press section 30 and spring arm lever section 28 perpendicularly to the bottom side 40 plane of the finger press section 30. The locking block 38 optionally may optionally have a concave ring seal slot 42 intermediate the locking block upper end 44 and the guide wire passage portion 49 in the locking block upper end 44. The ring slot 42 can have a central, innermost circumferential circular- or ring-shaped side 48 in a plane perpendicular to the plane of the opposed planar sides 34, 36 of the spring arm lever section 28.

Figure 6:
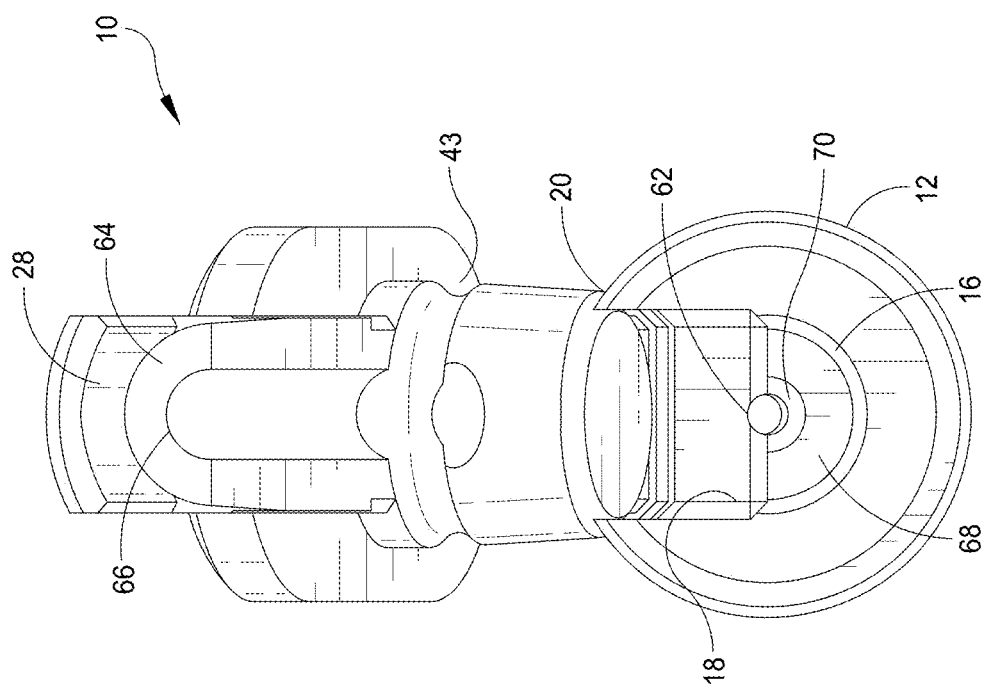
FIG. 6 is a grey scale plan view of the front end of the torque device of FIG. 1.
Figure 6A:
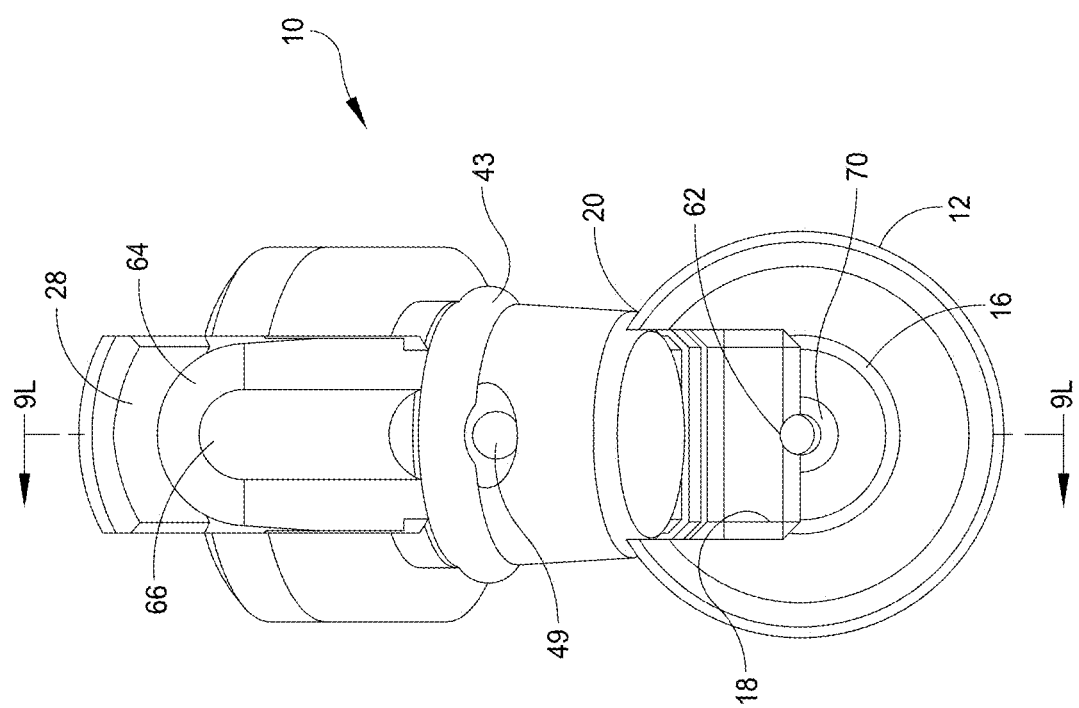
FIG. 6A is a black-and-white plan view of the front end of the torque device of FIG. 1.

When an optional seal ring (see 43 in FIG. 6A) is mounted in the ring seal slot 49 and torque device spring arm lever section 28 is depressed as explained infra, the seal ring's abutting contact with can prevent material, such as fluid for example, from leaking out of the upper end 44 of the locking block 38 when the material is injected through the lumen 62, including its guide wire passage portion 49, in the torque device 10.

The ring seal can be made of any suitable resilient and flexible material such as nitrile or ethylene-propylene-diene-monomer, but in some embodiments may be made of sterilizable material such as medical grade silicone. The ring seal may therefore be easily sterilized in ways well known to those skilled in sterilizing such materials.

Figure 4:
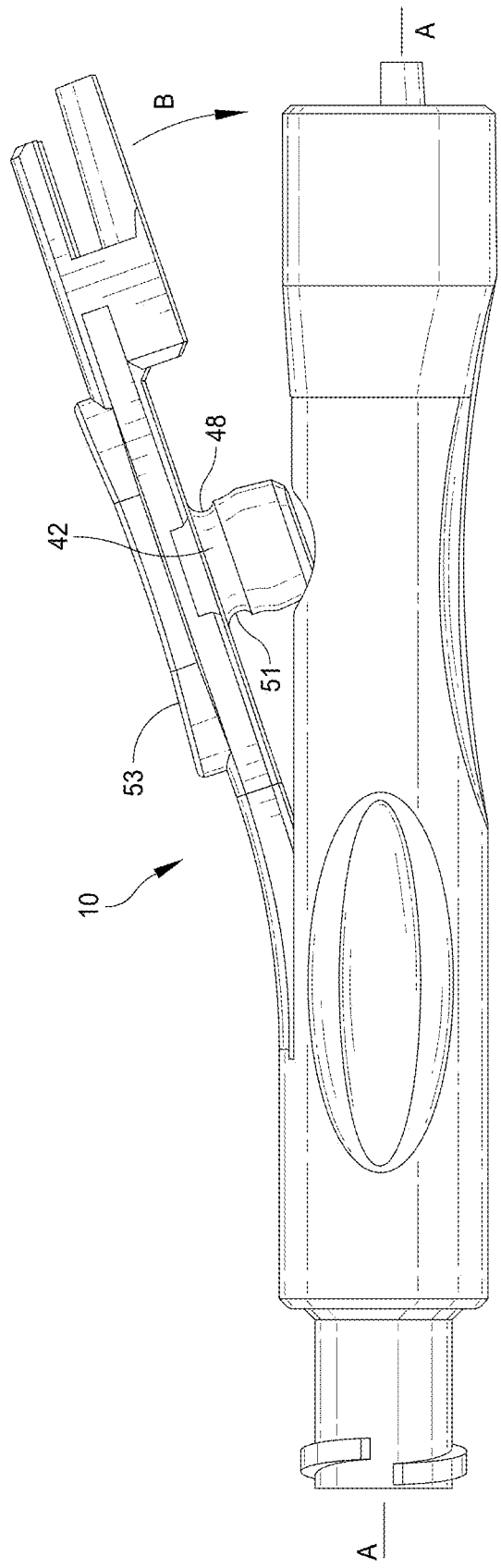
FIG. 4 is grey scale plan view of the second side of the torque device of FIG. 2.
Figure 4A:
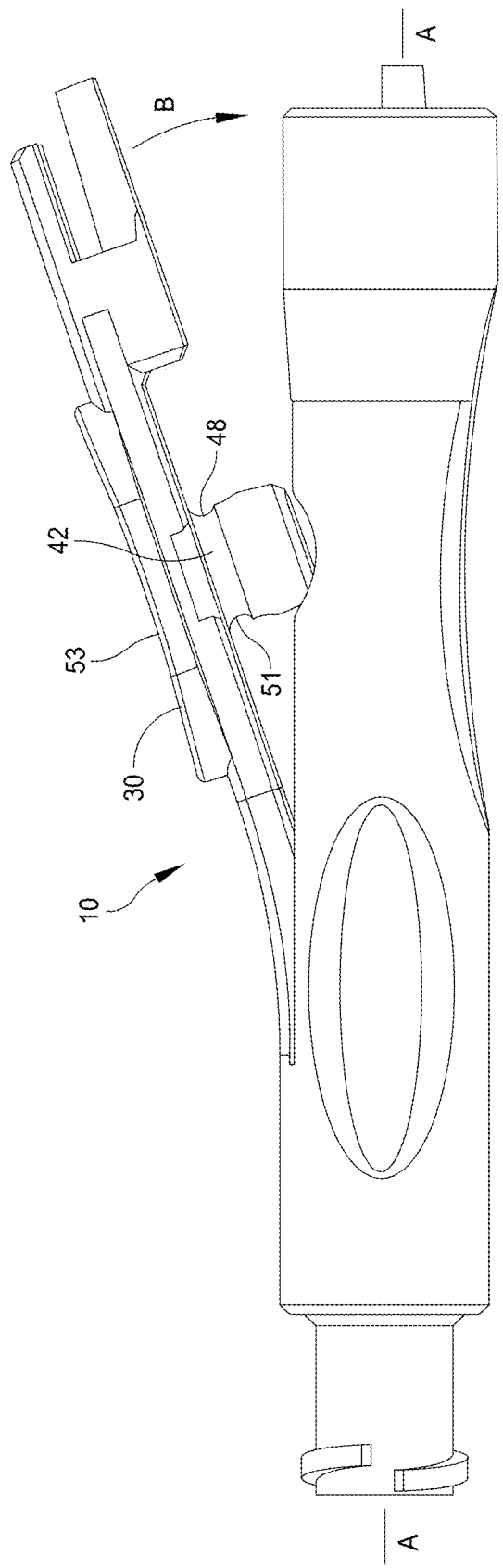
FIG. 4A is a black-and-white plan view of the second side of the torque device of FIG. 2.

With reference now to FIGS. 1, 1A, 2, and 5, the guide wire block 38 also has a wire guide passage portion 49 penetrating the ring seal slot 42 and passing through the guide wire block 38 to penetrate, as shown in FIGS. 4 and 4A, the ring seal slot's 42 opposite side 51 along a guide passage central axis in a plane also having axis A-A within the plane. The wire guide passage portion 49 can be sealed at both ends by mounting an optional, removable, flexible, resilient ring seal (not shown in FIGS. 1, 1A, 2, and 5) in the optional ring seal slot 42 so that the outer periphery of the inner side of the ring seal firmly abuts the entire inner periphery of the ring seal slot 42.

Referring now to FIGS. 4 and 4A, the finger press section 30 in the spring arm lever section 28 has an upper slightly concave surface 53. By applying finger pressure to the concave surface 53 toward axis A-A while securing the torque device 10 in position, the spring arm lever section 28 can rotate downwardly (see arrow B) toward axis A-A. In embodiments of the torque device 10 having, as shown in FIG. 3, the third finger-grip section 58, an operator (not shown) can perform this procedure by (i) having the thumb on one hand of the operator apply sufficient opposed pressure to the third or bottom finger-grip section 58 while (ii) having the forefinger on the operator's same hand apply opposed pressure to the spring arm lever section's finger press section 30, respectively.

Figure 2:
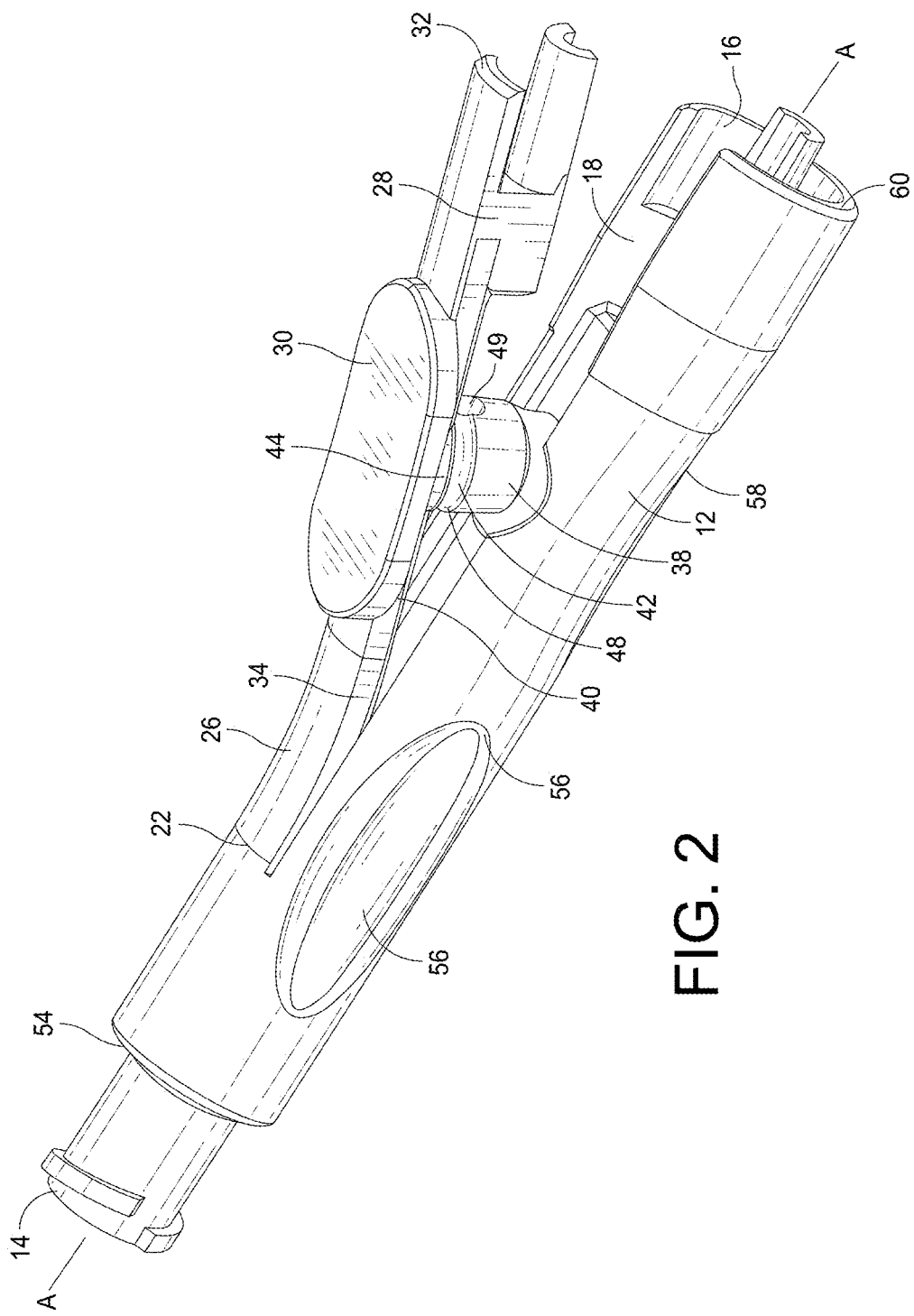
FIG. 2 is a grey-scale perspective view of second side of the torque device of FIG. 1 opposite the first side view of FIG. 1.
Figure 2A:
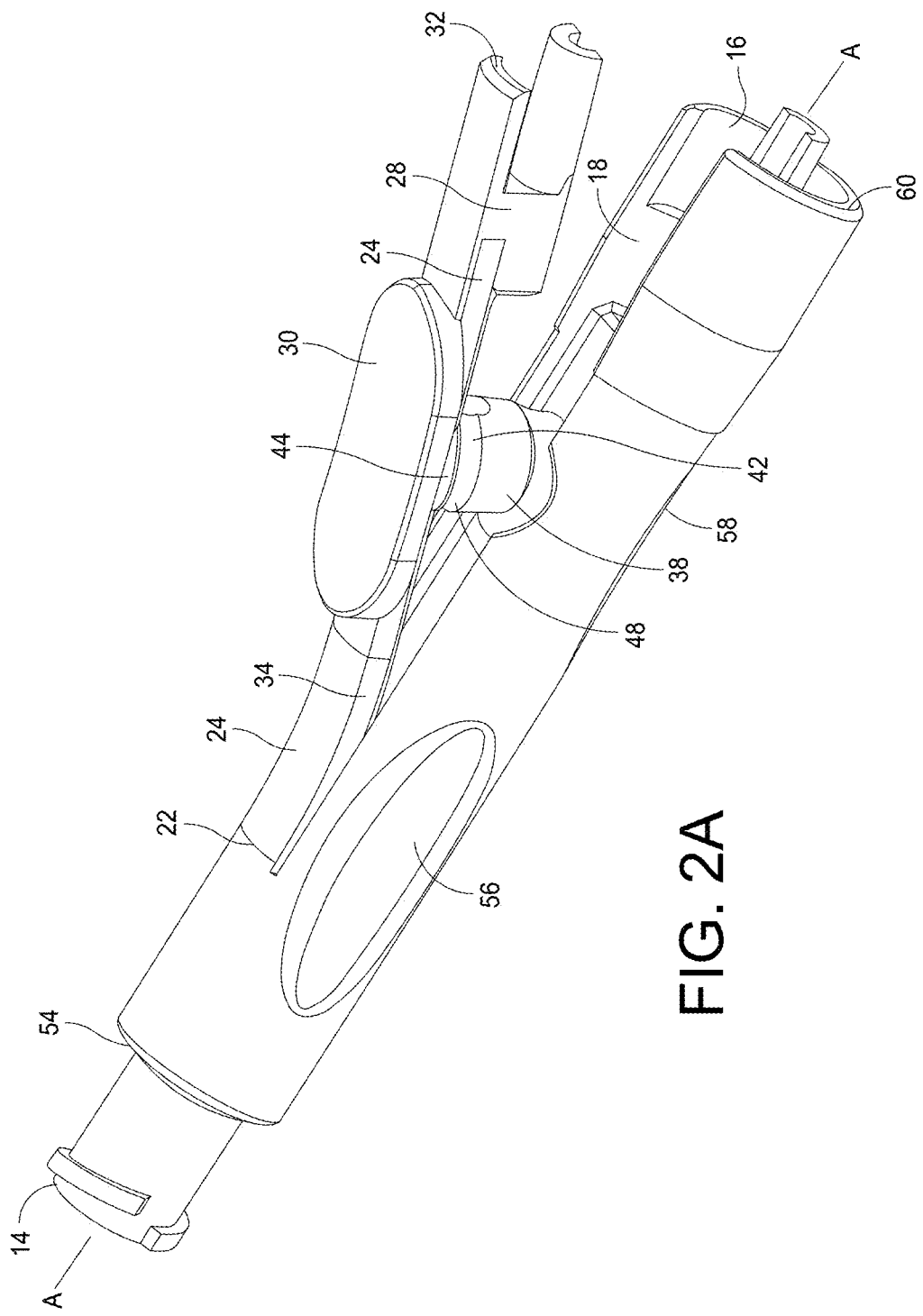
FIG. 2A is a black-and-white reversed perspective view of the second side of the torque device of FIG. 2.
Figure 3:
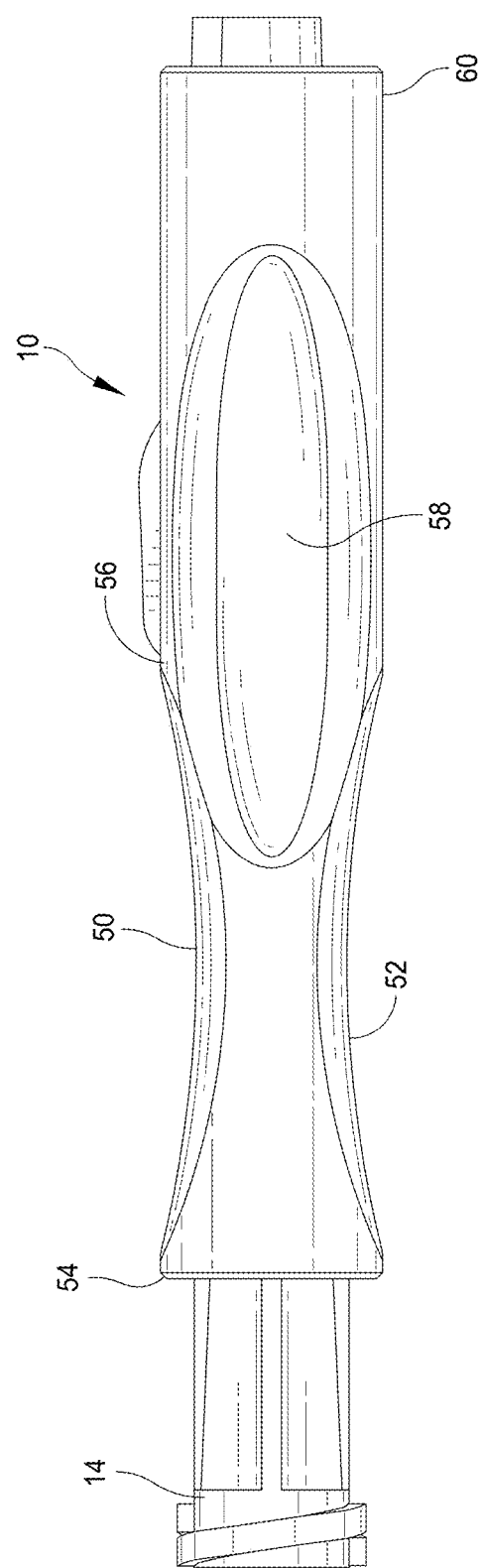
FIG. 3 is a grey scale perspective view of the bottom side of the torque device of FIG. 1.

With reference now to FIGS. 2, 2A, and 3, the outer periphery of the main body section 12 of the torque device 10 can optionally have a first concave hand-grip depression 50 optionally opposite and parallel to a second concave hand grip depression 52 with the spring arm passage 18 being intermediate and spaced equidistant from each of the first hand-grip depression 50 and the opposed second-hand grip depression 52. The first hand-grip depression 50 and second hand-grip depression 52 may extend from and laterally along a first central tubular end section 54 of the main body section 12 abutting the proximal main body end 14 toward, and optionally terminating adjacent, the middle portion 56 of the main body section 12.

The outer periphery of the main body section 12 can also optionally provide a third concave hand-grip depression 58. The third hand-grip depression 58 may penetrate the outer periphery of the main body section 12 opposite the spring arm channel 18 penetrating the main body section 12. The third hand-grip depression 58 also can extend from approximately adjacent, and if desired, spaced from and laterally along, a second central tubular end section 60 of the main body section 12 abutting the second main body end 16 toward the middle, and optionally terminating past, the middle portion 56 of the main body section 12 toward, but terminating spaced from, the first central tubular end section 60. The third hand-grip depression 58 is generally transverse to the first and second hand-grip depressions 50, 52, respectively.

Figure 1A:
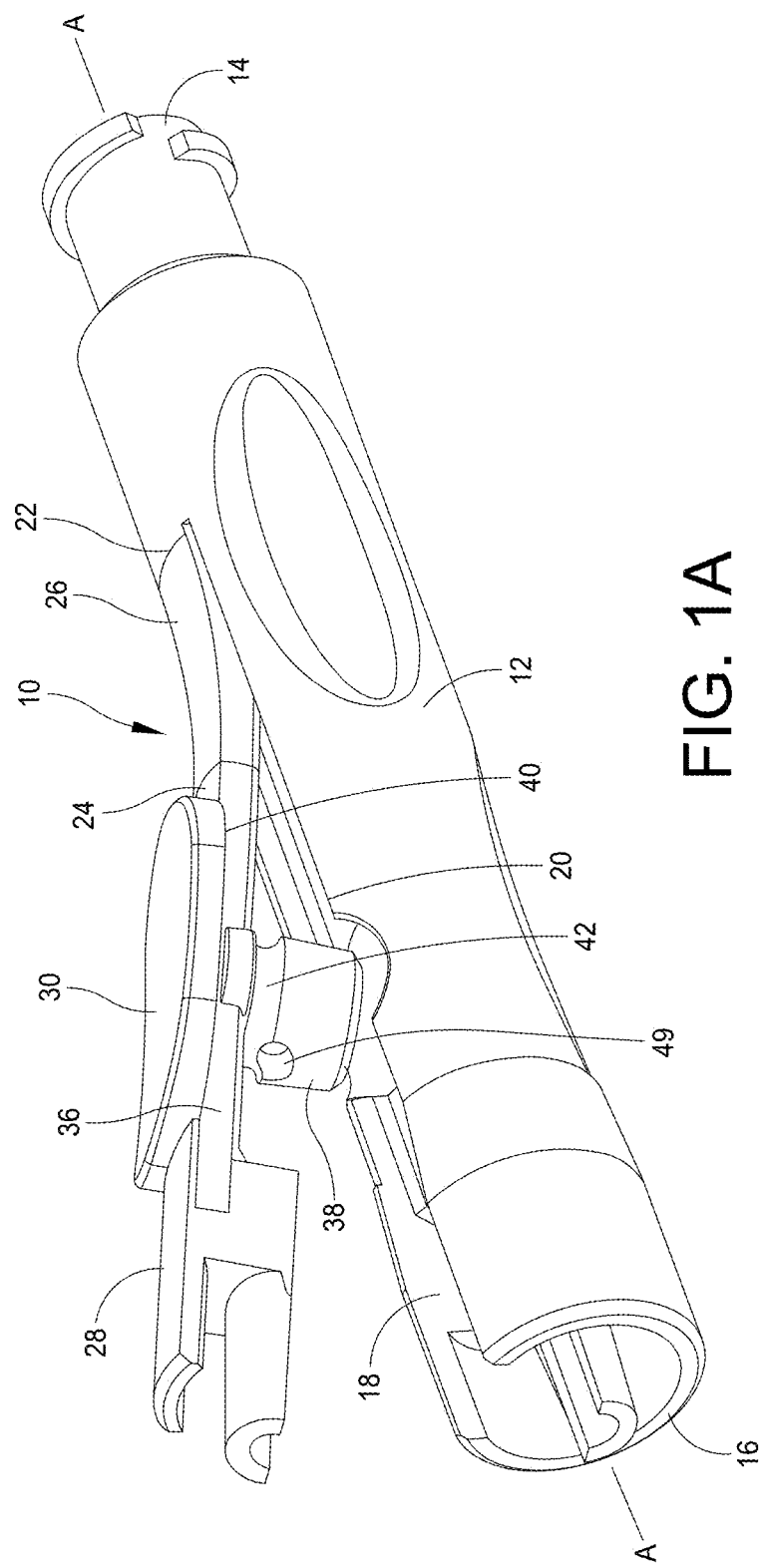
FIG. 1A is a black-and-white perspective view of the torque device of FIG. 1 showing contour lines.
Figure 7:
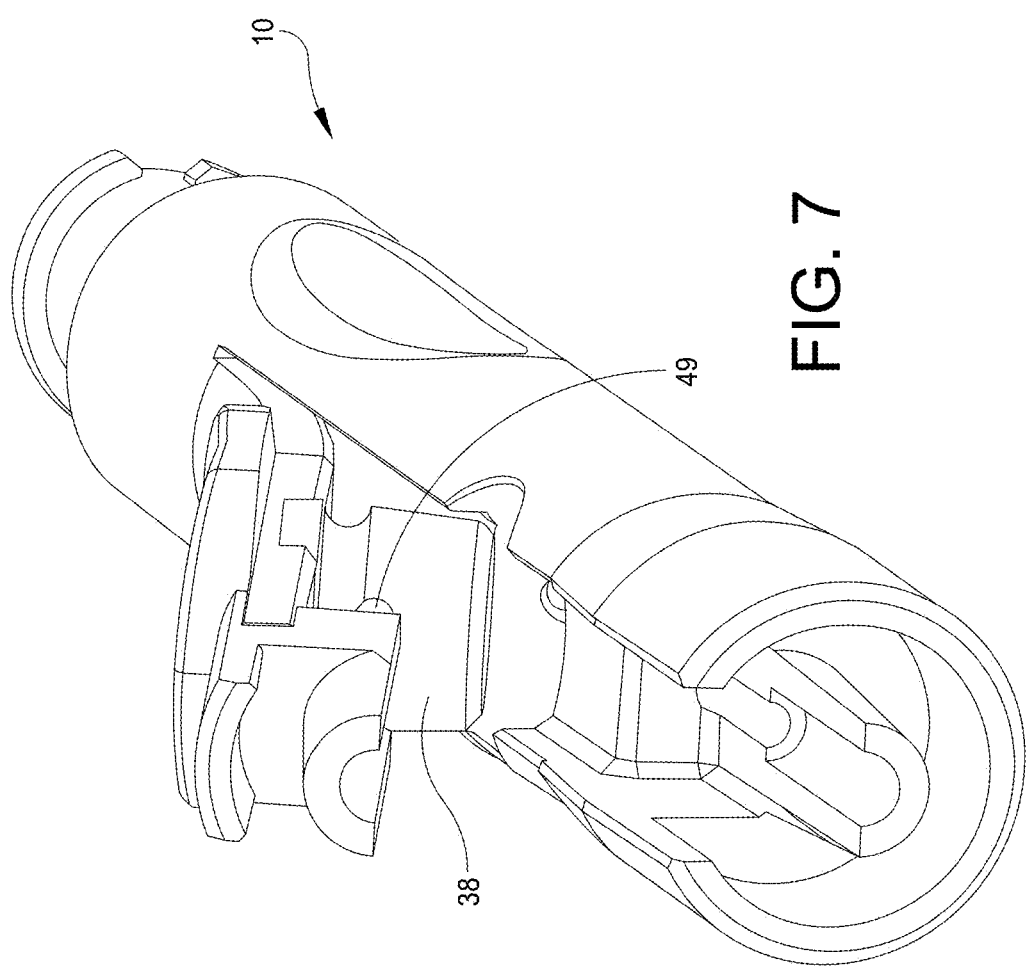
FIG. 7 is a black-and-white perspective view of the front end and first side view of the torque device of FIG. 1.

With reference now to FIGS. 6, 6A, 9, and 12, the main body section 12 of the torque device 10 has a main body wire guide passage and lumen 62 passing through, as shown in FIG. 1A for example, the main body section 12 along axis A-A of the main body section 12. In support of providing the wire guide passage 62 all along axis A-A through the torque device with the spring arm lever section 28 is rotated to fully penetrate the spring arm channel 18, the spring arm lever section has a novel C-shaped lever section lower sealing end 64 with the open face 66 of the C-shaped lever section lower end portion 64 facing toward and abutting a novel opposed C-shaped spring arm channel sealing end portion 68 and its open face 70 extending along the spring arm channel 18 adjacent, and terminating at, the second main body end 16 in the main body section 12. The opposed and thereby abutting C-shaped lever section lower end 64 and C-shaped spring arm channel end portion 68 can thereby cooperatively provide a widened spring channel passage 72 (see FIG. 9) so that a guide wire (see FIG. 13 and associated text) and other material, such as a fluid for example, may pass through the spring channel passage 72 and, if sufficiently wide, other wire passage sections passing through the torque device 10 such as, for example, the wire guide passage 62 including, with reference to FIGS. 7, 9, and 12, the guide wire passage portion 49 in the guide wire block 38.

Figure 8:
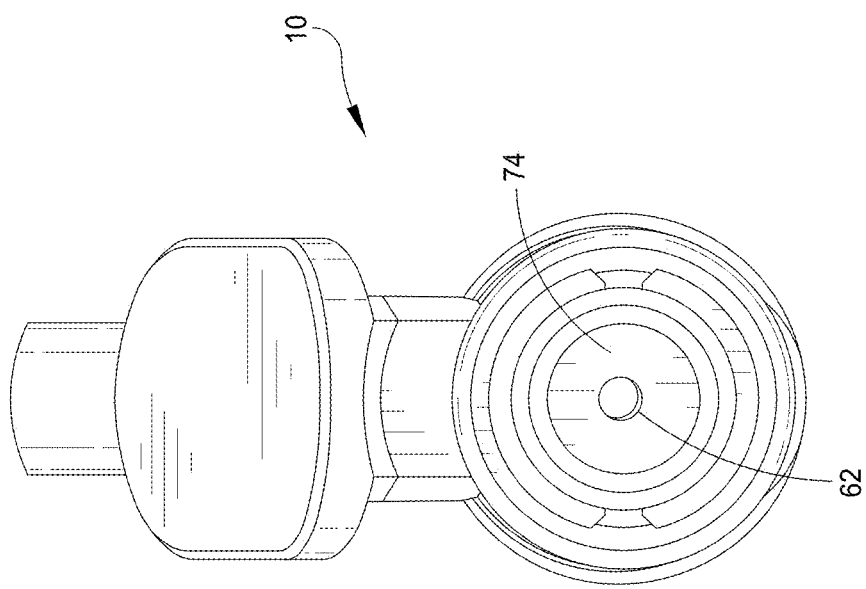
FIG. 8 is a grey scale plan view of the back end of the torque device of FIG. 1.
Figure 8A:
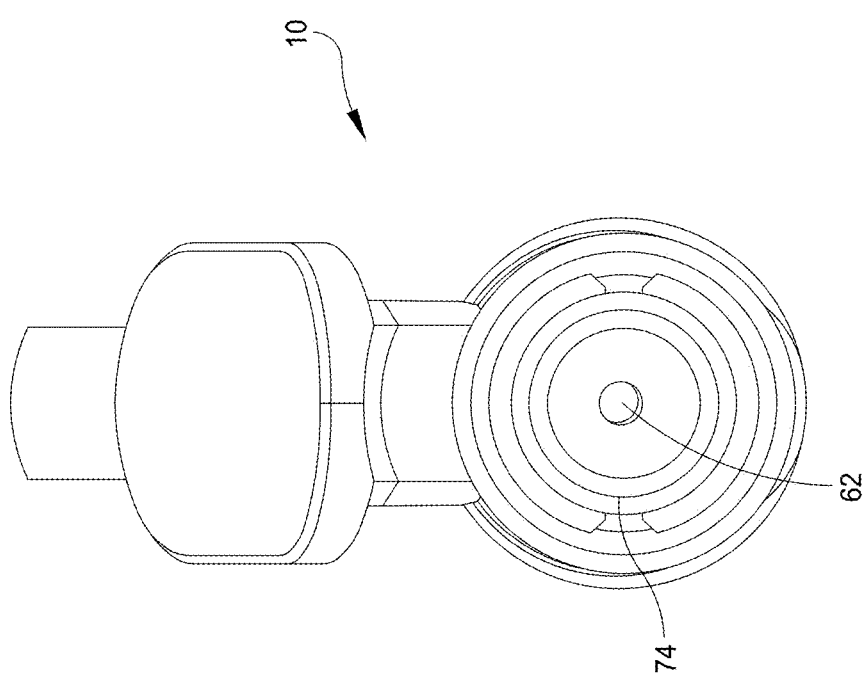
FIG. 8A is a black-and-white plan view of the back end of the torque device of FIG. 1.

With reference to FIGS. 8 and 8A, the proximal end 14 of the torque device 10 can have a concave widened guiding section 74 surrounding the guide wire passage 62. The concave guiding section 74 can help steer an operator's insertion of a guide wire (see FIG. 13 and associated text) or other component, such as a catheter, into the guide wire passage 62 (80 in FIG. 13).

Figure 5:
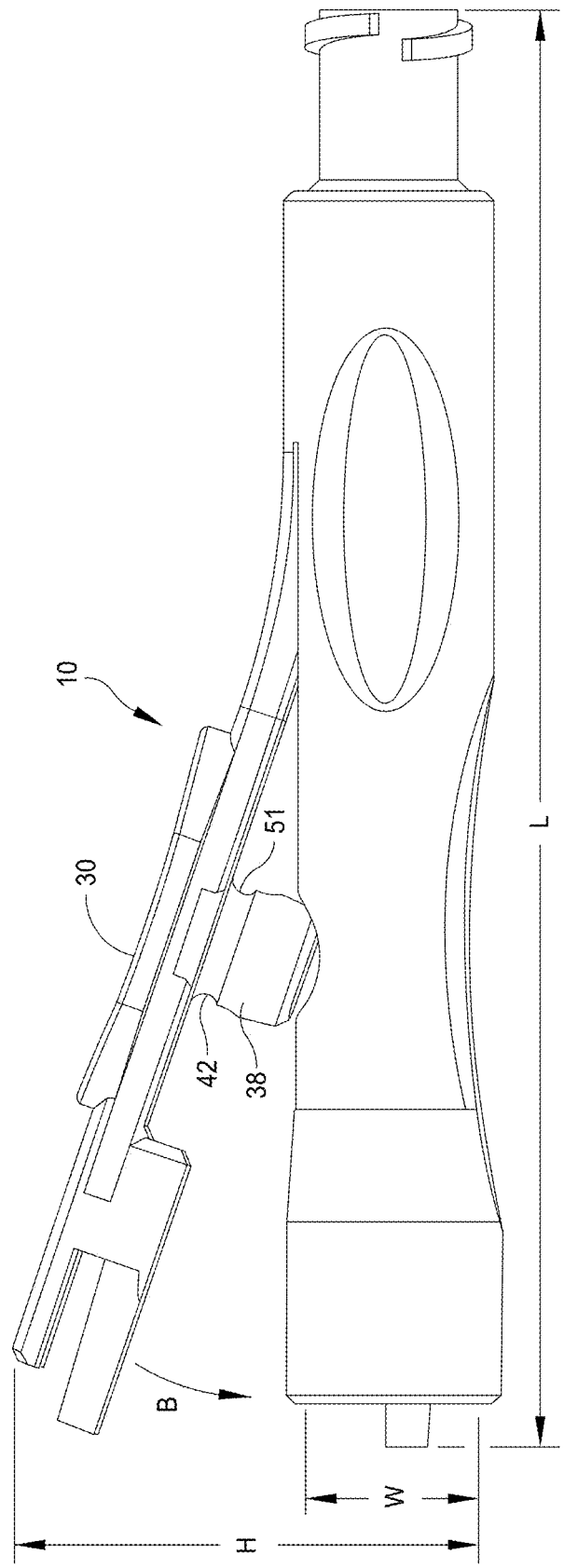
FIG. 5 is black-and-white view of the first side of the torque device of FIG. 1.

With reference to FIG. 5, one embodiment of the present torque device 10 can have an axial length, L, of or about 2-3 inches, a main body diametral width, W, of or about 0.3 to 0.4 inches, and a free state over height, H, of or about 0.6 to 0.9 inches.

Figure 10:
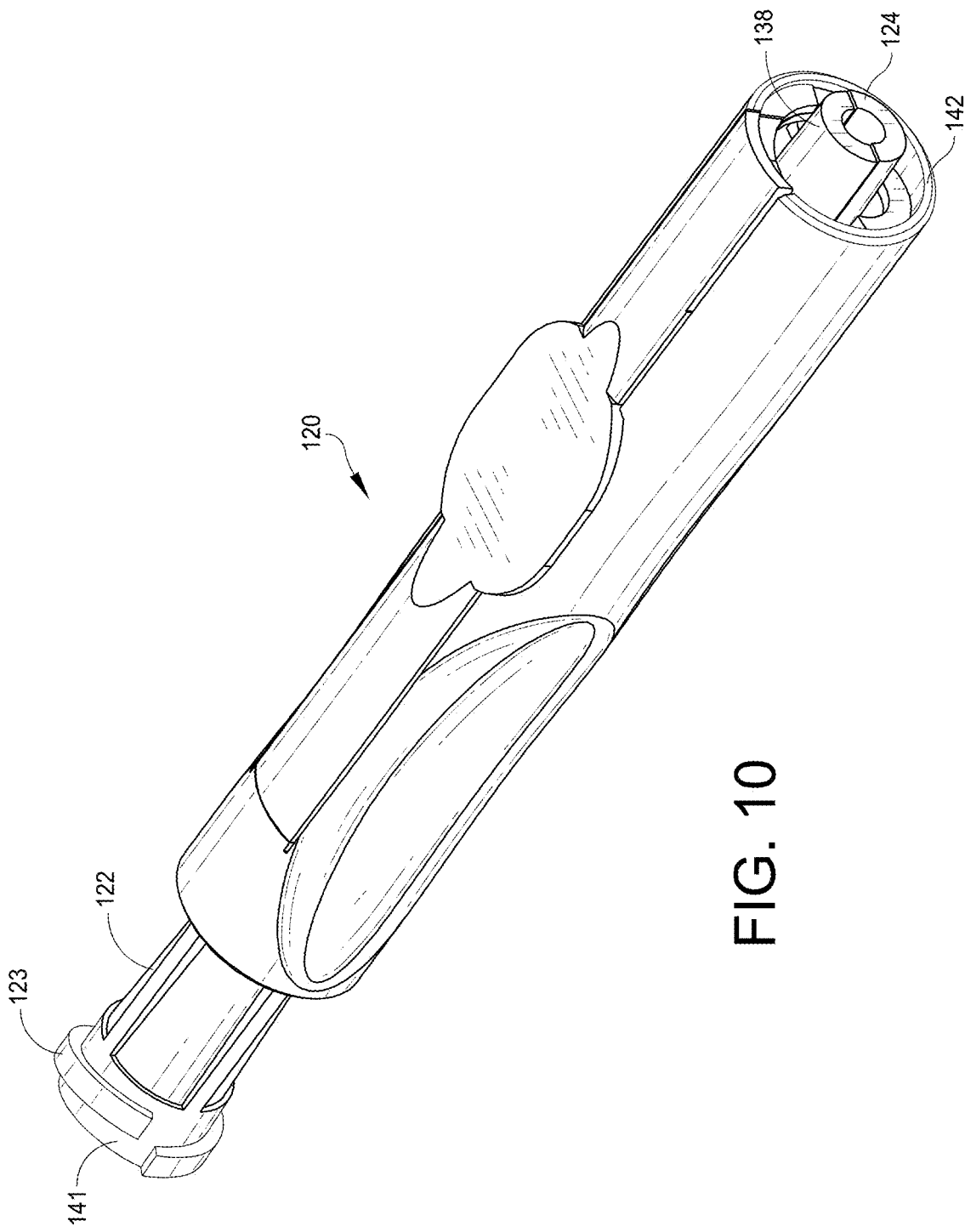
FIG. 10 is a grey-scale perspective second side view of a torque device similar to the torque device of FIG. 1 but having a longer back end female Luer lock section and with its upper spring arm in a closed, depressed state.
Figure 11:
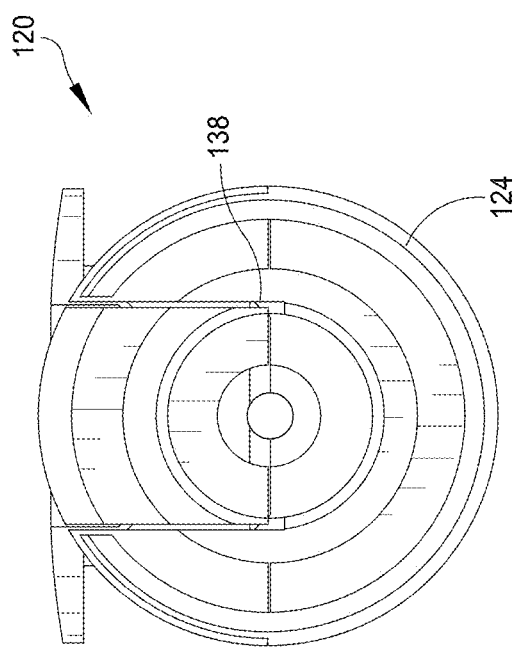
FIG. 11 is a gray scale plan view of the front end of the torque device of FIG. 10.

With reference now to FIGS. 10, 11, 15, and 16, a second alternative torque device 120 is identical to the embodiment of FIG. 1 except that it includes (i) a longer female back end 122 (optionally providing female Luer lock structure 123) and (ii) a male Luer lock front end 124 cooperatively provided by (a) an upper half male Luer lock 124 extending the bottom side 126 of the front section 128 of the spring arm 130 and (b) a lower half male Luer lock 132 provided in a Luer lock channel 134 penetrating the front end 136 of the main body section 138 of the second alternative torque device 120. As shown in FIGS. 10 and 11, a unitary male Luer lock section 138 results from depressing the spring arm 130 to cause the upper half male Luer lock 124 to abut or become closely adjacent to the lower half male Luer lock 132.

Figure 13:
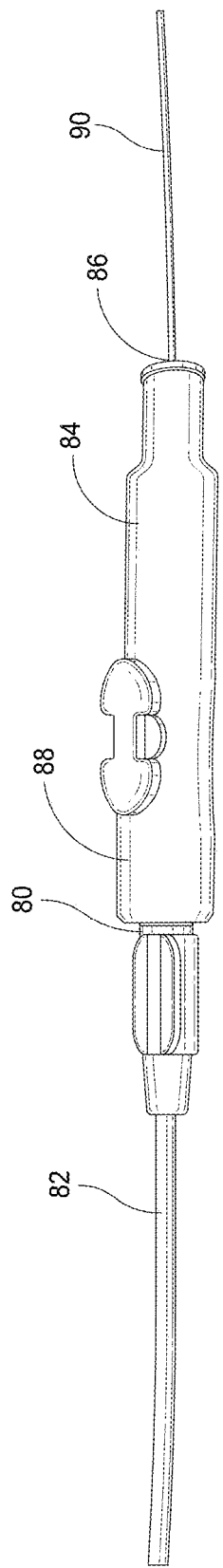
FIG. 13 is a photograph of a prototype embodiment of the present torque device with its Luer lock in its front end secured to a mating Lure lock back end in a catheter with a guide wire passing through the integrated torque-device/catheter unit.

With reference now to FIGS. 10 and 13, when the front male Luer lock (concealed in FIG. 13) interlocks with a female Luer lock (concealed in FIG. 13) in the proximal end 80 of a catheter, the male Luer lock secures the spring arm and opposed spring arm channel in the closed position of FIGS. 10 and 11. In this closed position, the torque device lumen 140 extends from the back or proximal end 141 to the front or distal end 142 of the torque device 120; and as shown in FIG. 13, the interconnected torque device 84 and catheter 82 (a torque-device/catheter unit 88) cooperatively provide a torque-device/cather lumen 86 extending through both the torque device 84 and catheter 82 and through which a guide wire 90 or other material, such as fluid (not shown), may freely pass in either direction through the torque-device/catheter lumen 86. Similarly, the torque-device/catheter unit 88 may be freely moved backward or forward along the guide wire 88 penetrating the torque-device/catheter lumen 86.

Figure 12:
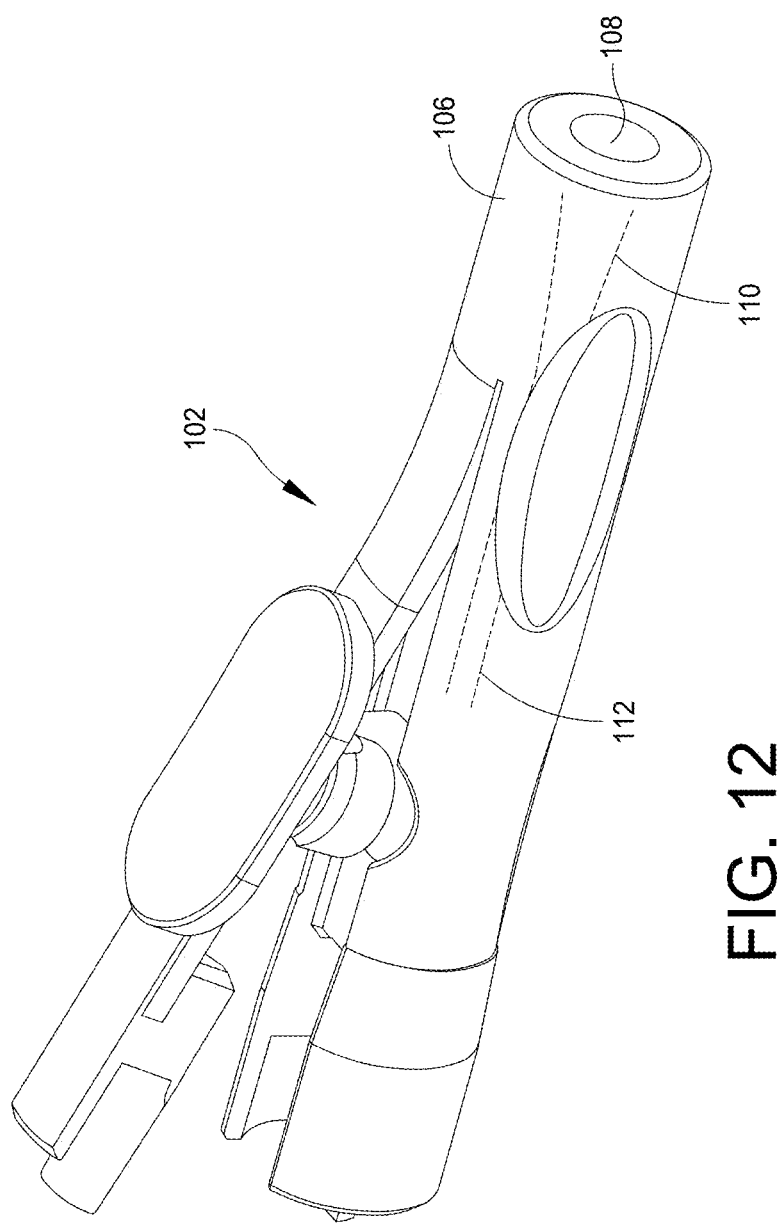
FIG. 12 is a black-and-white perspective view of a second alternative embodiment of the present torque device with a widened front end section and an enlarged tubular back end for introduction of a guide wire, catheter, or other material into the torque device lumen at its back end.

Turning now to FIG. 12, a first alternative embodiment of the present torque device 92 can have a widened back tubular end 106 with a widened lumen entrance 108 for easy introduction of a guide wire (not shown in FIG. 12) into the lumen entrance 108. The interior portion 110 of the Lumen entrance 108 may be tapered to communicate with a narrower interior lumen passage 112. The torque device can have yet differently configured back ends as desired to secure to other structures, such as, for example. a fluid supplying apparatus.

Figure 9:
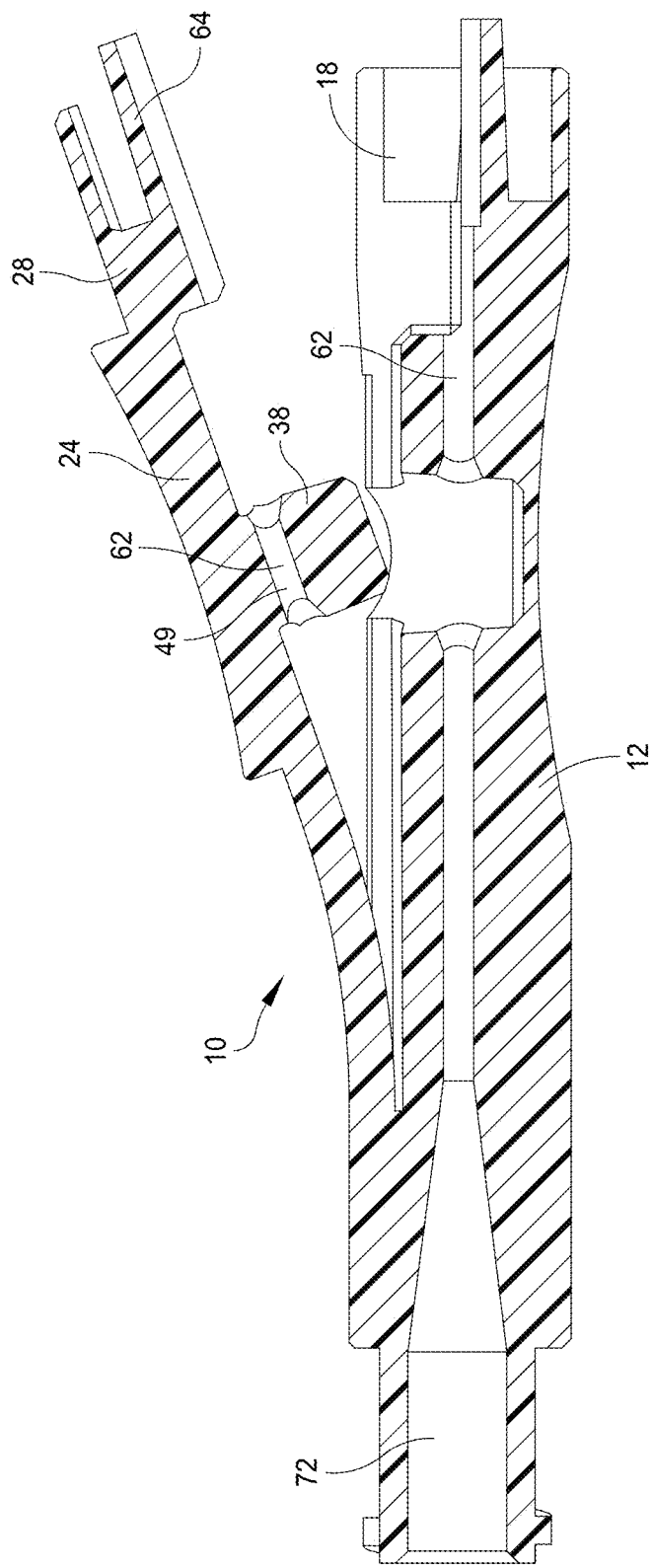
FIG. 9 is a grey-scale cross-sectional view of the torque device of FIG. 1 taken along section line 9L-9L of FIG. 6.
Figure 14:
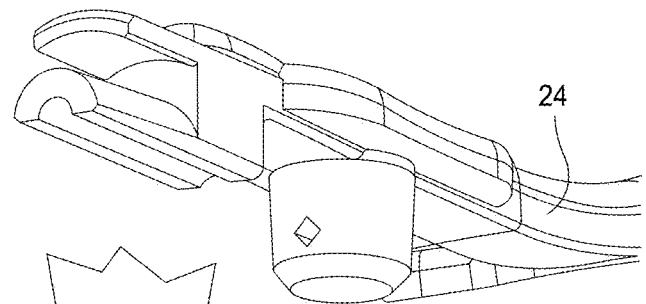
FIG. 14 is a perspective view of three torque device spring arms having differently shaped guide wire passages passing through the spring arm locking blocks, respectively.
Figure 14:
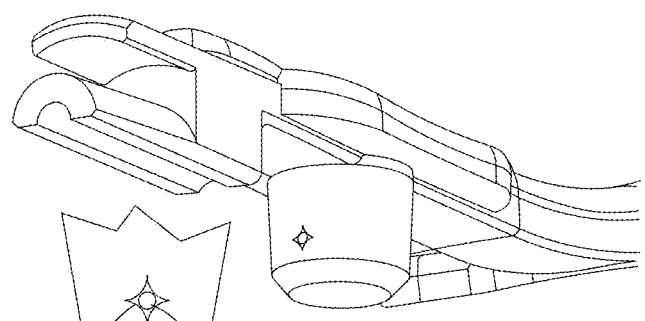
Figure 14:
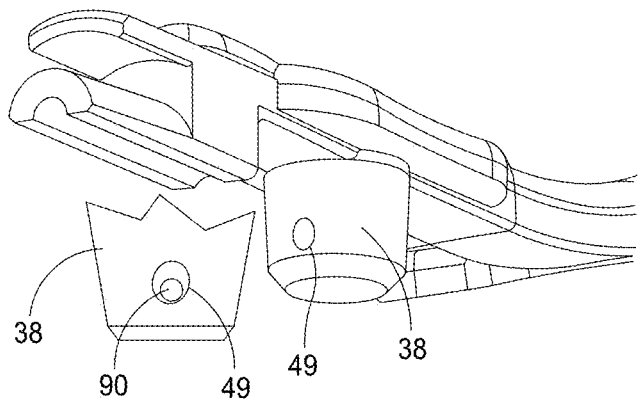
Figure 15:
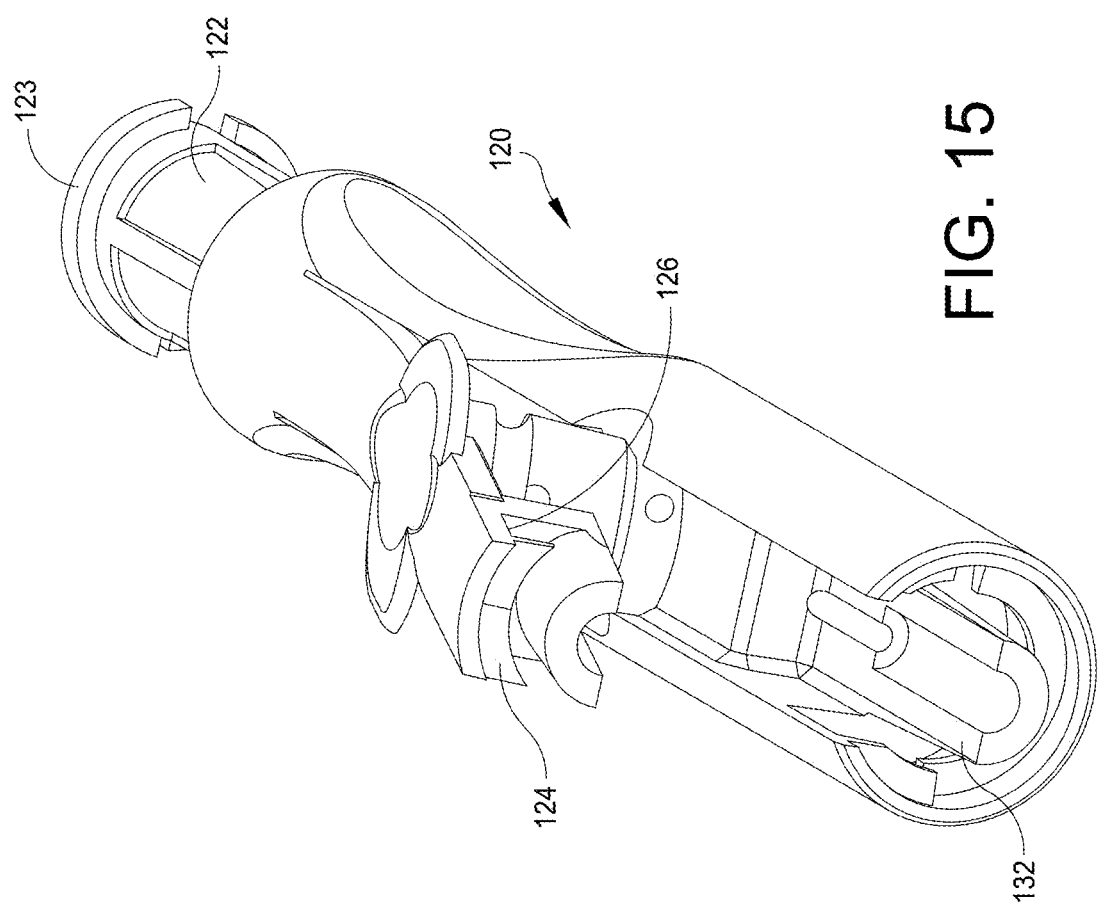
FIG. 15 is a black-and-white perspective view of the torque device of FIG. 10 having a Luer lock in its front end.
Figure 16:
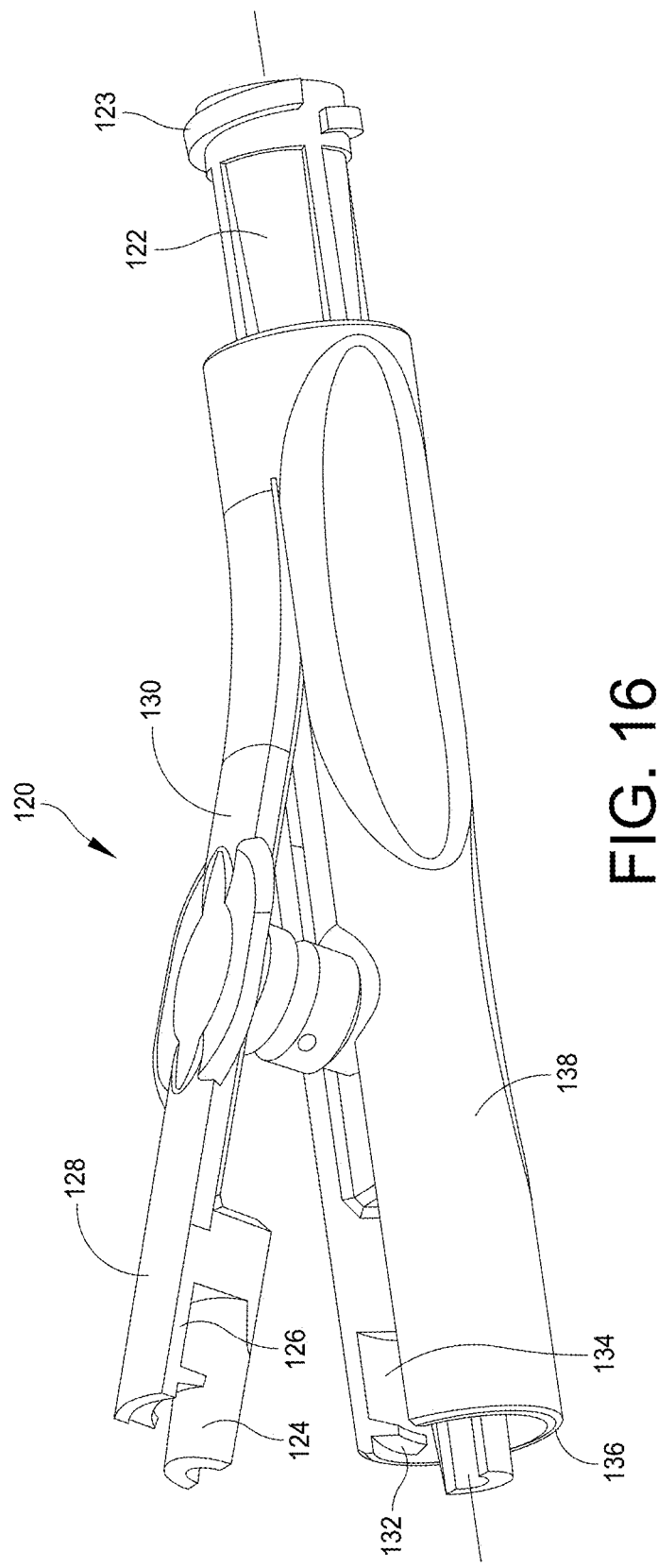
FIG. 16 is a black-and-white perspective view of the torque device of FIG. 10 having a Luer lock in its front end.

With reference to FIGS. 9 and 14, the wire passage portion 49 may have any of many differing configurations, such as a rectangular interior periphery 114 or star-shaped interior periphery 116, in order to increase their gripping contact with the guide wire when the spring arm is further depressed by the operator (not shown).

The torque device, such as of FIGS. 1-16, may be molded or 3D-printed to provide a one-piece or unitary torque device. Such a torque device, or its components if made and assembled otherwise, can be made of any suitable material such as plastic. Suitable plastics may include nylon or high density polyethylene.

Some embodiments of the present torque device may be made of sterilizable material such as sterilizable polytetrafouroethylene. Some embodiments of the present torque device may therefore be easily sterilized in ways well known to those skilled in sterilizing devices made of such materials.

As explained in greater detail above, the prior art torque device designs have typically required that the torque device be slid or "walked" on and off of the angiographic wire separate from the catheter with any catheter exchange or introduction. With the prior art fixed spring torque device, for example, moving the torque device over the wire requires that the operator actively depression of the spring; and accidental release of spring-depressing tension can cause the device to engage the wire, which can result in loss of desired wire access positioning.

In use of the present torque device, such as the embodiments of torque devices shown in the accompanying FIGS. 1-16, an operator depresses the torque device's front spring arm and docks incorporation of the front sealing extension in the spring arm into the torque device's mating front end (having for, example, a male Luer lock) to a catheter proximal end (having, for example, a mating female Luer lock). This docking operation causes the spring arm to be held in the docked, interlocked position with the catheter, providing an open lumen configuration from the back end through to the front end of the torque device (that is, providing a linear lumen or channel through the entire length of the torque device along lumen or channel axis A-A as in FIGS. 1 and 1A) with the lumen then continuing from the front end of the torque device through the back or proximal end of the catheter through to the front or distal end of the catheter. Upon docking of the torque device, the operator can cease applying pressure to the torque device spring arm and perform a procedure with the torque-device/catheter.

When the front end of the torque device is docked, and thus interlocked to, a mating structure in the proximal end of the catheter (such as, for example, a female Luer lock) in the proximal end of the catheter, the resulting interlocked torque-device/catheter can thus move as a unit, including along a guide wire penetrating the lumen of the torque-device/catheter. This allows free movement of the interlocked torque-device/catheter as a unit with one hand and without further operator effort to depress a spring arm or other type of structure during catheter insertion or exchange. In addition, interlocking docking of the torque device to the catheter can facilitate rapid wire advancement of the torque device and catheter as unit when a target vessel has been selected. Embodiments of present torque device can thus substantially reduce time, labor, and hospital resource consumption in endovascular operations involving introduction and advancement of structures such as catheters or guidewires into blood vessels. This docking procedure may be reversed to undock the torque device from the catheter.

When the torque device is mounted to a guide wire and not secured to a catheter and the torque device's spring arm has no pressure applied to it, the spring arm is biased to rotate to its free state away from the spring arm channel in the main body section of the torque device. This causes the guide wire passage portion in the spring arm's locking block to move outwardly from the spring arm channel and away from alignment with the adjacent portion of the main body wire guide lumen. This in turn causes the guide wire passage portion and the adjacent wall of the main body wire guide lumen surrounding the guide wire to cooperatively abut, grip, and secure the guide wire in position in the guide wire passage portion in the locking block. Conversely, depressing the spring arm with one hand causes the main body wire guide lumen and locking block wire guide passage portion to align and release the guide wire so that it is free to move through the torque device lumen, such as by operator use of one hand to depress the spring arm and the other hand to grip guide wire external to the torque device and move the guide wire through the torque device lumen jointly provided by the main body section and spring arm pressed or otherwise forced into the spring arm channel in the main body section. The same procedure can be performed with the other torque device embodiments shown in the accompanying FIGS. 10-16.

In some embodiments, the optional o-ring seal around the spring arm clamping or locking block can seal the area below the ring seal, including the guide wire lumen 62 in the torque device, to allow fluids or other materials to be injected through the torque device into an associated catheter. Similarly, in some embodiments of the torque device, the optional back end female Luer lock end may be penetrated by, and sealingly interlock with, a mating male Luer lock end (not shown) in an apparatus supplying such fluid or material (not shown). These features can, for example, allow for catheter flushing or injection of contrast for angiography via the catheter with the torque device in place.

All dimensions disclosed above can be varied for varying circumstances, uses, and objects. They may be varied by ranges of plus or minus 1% through up to 40% with the ranges in some embodiments varying by differing amounts for differing aspects of a given torque device and torque device application. Some embodiments may vary in size from 40% greater to as large as desired, such as 5000% greater or even more for large systems.

The foregoing detailed description has described some specific embodiments. However, the illustrative discussions above are not intended to be exhaustive or to limit the invention to the precise forms disclosed. Many modifications and variations are possible in view of the above teachings.

Unless otherwise noted, the terms "a" or "an," as used in the specification and claims, are to be construed as meaning "at least one of." In addition, for ease of use, the words "including" and "having," as used in the specification and claims, are interchangeable with and have the same meaning as the word "comprising." In addition, the term "based on" as used in the specification and the claims is to be construed as meaning "based at least upon." Also, as used herein, including in the claims, "or" as used in a list of items prefaced by "at least one of" indicates a disjunctive list such that, for example, a list of "at least one of A, B, or C" means A or B or C or AB or AC or BC or ABC (i.e., A and B and C).

Unless otherwise indicated, all numbers or expressions, such as those expressing dimensions, physical characteristics, and the like, used in the specification are understood to be modified in all instances by the term "approximately," meaning the numbers or expressions can be increased or decreased by up to 10%. All disclosed ranges are to be understood to encompass and provide support for claims that recite any and all subranges or any and all individual values subsumed by each range.

For example, a stated range of 1 to 10 should be considered to include and provide support for claims that recite any and all subranges or individual values that are between and/or inclusive of the minimum value of 1 and the maximum value of 10; that is, all subranges beginning with a minimum value of 1 or more and ending with a maximum value of 10 or less (e.g., 5.5 to 10, 2.34 to 3.56, and so forth) or any values from 1 to 10 (e.g., 3, 5.8, 9.9994, and so forth).

Finally, it is to be understood that embodiments of the present torque device and methods of use have been described in association with human patients. Embodiments of the present device and methods can be utilized with other creatures, such as animals and possibly other environments and applications as well.

What is claimed is:

1. A torque system of the type that may be used to move an element in a blood vessel, the torque system comprising a catheter and a torque device, the torque device comprising in combination:
   A. a main body section having a first lumen section extending within the main body section from a first end of the main body section toward an opposing second end of the main body section;
   B. a spring arm having a first spring arm end section extending from the main body section and a second spring arm end section opposite the first spring arm end section and biased away from the main body section, the second spring arm end section having at least a portion of a second spring arm lumen section depressable toward the main body section, the at least a portion of the second spring arm lumen section penetrates the main body section and the second spring arm end section and second end of the main body section being interlocked with a catheter,
   whereby the element is movable through the first lumen section, second spring arm lumen section, and a catheter lumen in the catheter and the torque device and catheter can be interlocked and moved as a unit with respect to the element when inserted through the first lumen section, second spring arm lumen section, and the catheter lumen.

2. The torque device of claim 1 wherein the main body section includes a spring arm channel matingly receptive of the second spring arm end section.

3. The torque device of claim 1 wherein the first spring arm end section includes a seal mounting section receptive of a resilient seal.

4. The torque device of claim 3 wherein the second spring arm lumen section and second end in the main body section are moveable with respect to each other to cooperatively provide a Luer lockable end.

5. The torque device of claim 4 wherein the Luer lockable end is a male Luer lockable end.

6. The torque device of claim 3 also comprising a resilient seal on the spring arm.

7. The torque device of claim 1 wherein the second end of the main body section includes at least a portion of a second end main body lumen section cooperatively abuttable with the second spring arm lumen section.

8. The torque device of claim 1 wherein the second spring arm lumen section and second end main body lumen section in the main body section are cooperatively mountable in a proximal end of the catheter.

9. The torque device of claim 1 wherein the second spring arm lumen section and second end in the main body section are moveable with respect to each other to cooperatively provide a main body lumen.

10. The torque device of claim 1 wherein the second spring arm end section also has a finger pad on an exposed side of the spring arm opposite a main body penetrating side on the second spring arm end section.

11. The torque device of claim 1 wherein the first end of the main body section includes a male Luer lockable end.

12. The torque device of claim 1 wherein the at least a portion of a second spring arm lumen section penetrates the main body section and the second spring arm end section and second end of the main body section are interlocked with a mating proximal end of a catheter.

13. The torque device of claim 12 wherein second spring arm end and second end of the main body section cooperatively provide a Luer lock end.

14. The torque device of claim 12 wherein the first lumen section extending within the main body section includes a female Luer lock section.

15. A torque-device/catheter of the type that may be used to move an element in a blood vessel, the torque-device/catheter comprising in combination:
   A. a main body section having a first lumen section extending within the main body section from a first end of the main body section toward an opposing second end of the main body section; and
   B. a spring arm having a first end section extending from the main body section and a second end section opposite the first end section and biased away from the main body section, the second end section having at least a portion of a second lumen section depressable toward the main body section, the second end section and main body section being interlocked to a proximal end of a catheter.

16. The torque device/catheter of claim 15 wherein the main body section includes a spring arm channel matingly receptive of the second end section in the spring arm.

17. The torque device/catheter of claim 16 wherein at least a portion of the second spring arm end section penetrates the main body section and the second spring arm end section and second end of the main body section are interlocked with the catheter,
   whereby the interlocked torque device and catheter are moveable as a unit with respect to an element movable through the first lumen section, the second lumen section, and a catheter lumen in the catheter.

18. The torque device of claim 17 wherein the at least a portion of the second lumen section penetrates the main body section and the second lumen section and second end of the main body section are interlocked with a mating proximal end of the catheter.

19. The torque device of claim 18 wherein second end section in the spring arm and second end of the main body section cooperatively provide a Luer lock end.

20. The torque device of claim 19 wherein the first lumen section extending within the main body section includes a Luer lock section.

21. The torque device/catheter of claim 15 wherein the second end section in the spring arm includes a seal mounting section receptive of a resilient seal.

22. The torque device/catheter of claim 15 wherein the second end of the main body section includes at least a portion of a second main body lumen section cooperatively abuttable with the second lumen section in the spring arm.

23. The torque device/catheter of claim 22 wherein the second lumen section in the spring arm and second lumen section in the main body section are moveable with respect to each other to cooperatively provide a main body lumen.

24. The torque device/catheter of claim 23 wherein the second lumen section in the spring arm and second lumen section in the main body section cooperatively provide a Luer lockable end.

25. The torque device/catheter of claim 24 wherein the Luer lockable end is a male Luer lockable end.

26. The torque device/catheter of claim 22 also comprising a resilient seal on the spring arm.

27. The torque device/catheter of claim 15 wherein the second lumen section in the spring arm and a second lumen section in the main body section are cooperatively mountable in a proximate end of the catheter.

28. The torque device/catheter of claim 15 wherein the second spring arm end section also has a finger pad on an exposed side of the spring arm opposite a main body penetrating side on the second spring arm end section.

29. The torque device/catheter of claim 15 wherein the first end of the main body includes a Luer lockable end.

* * * * *